US012754178B2

(12) United States Patent
Kapse et al.

(10) Patent No.: US 12,754,178 B2
(45) Date of Patent: Oct. 6, 2026

(54) NON-INVASIVE METHOD AND SYSTEM FOR DETECTING QUALITY OF PACKAGED MILK

(71) Applicant: Tata Consultancy Services Limited, Mumbai (IN)

(72) Inventors: Shrikant Arjunrao Kapse, Pune (IN); Priya Kedia, Pune (IN); Jayita Dutta, Pune (IN); Shankar Balajirao Kausley, Pune (IN); Parama Pal, Pune (IN); Parijat Dilip Deshpande, Pune (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 698 days.

(21) Appl. No.: 18/319,077

(22) Filed: May 17, 2023

(65) Prior Publication Data

US 2023/0384281 A1 Nov. 30, 2023

(51) Int. Cl.
*G01N 33/04* (2006.01)
*G01N 27/22* (2006.01)
(Continued)

(52) U.S. Cl.
CPC ............. *G01N 33/04* (2013.01); *G01N 27/22* (2013.01); *H04B 5/22* (2024.01); *H04B 5/70* (2024.01)

(58) Field of Classification Search
CPC ...... G01N 27/22; G01N 27/221; G01N 33/04; H04B 5/22; H04B 5/70; H04B 5/73; H04N 9/455
See application file for complete search history.

(56) References Cited

U.S. PATENT DOCUMENTS 9,563,833 B2 2/2017 Swager et al.

FOREIGN PATENT DOCUMENTS

CN 105868995 B 5/2021
KR 20140039833 A 4/2014

OTHER PUBLICATIONS

Potyrailo et al "RFID sensors based on ubiquitous passive 13.56-MHz RFID tags and complex impedance detection". Wirel. Commun. Mob. Comput., 9: 1318-1330. https://doi.org/10.1002/wcm.711 (Year: 2009).*

(Continued)

*Primary Examiner* — Jennifer Wecker
*Assistant Examiner* — Jonathan Bortoli
(74) *Attorney, Agent, or Firm* — Finnegan, Henderson, Farabow, Garrett & Dunner, LLP

(57) ABSTRACT

Milk is consumed in large quantities across the world and quality of milk is important to consumer. Multilayer packaging is one of solution to maintain quality of milk for prolonged period. However, quality of milk may change due to issues in handling, transportation, environment, and packaging. Currently available techniques fail to detect milk quality when packaging is opaque. Hence, common methods that are used for detecting quality of milk cannot be easily used over packaged milk. Present application provides non-invasive method and system for detecting quality of packaged milk. More specifically, system uses a sensing technique enabled in a capacitive Near-field communication (NFC) tag and an NFC enabled device for detecting quality of the packaged milk in real-time. In particular, the capacitive NFC tag is configured to provide milk quality information on NFC enabled device when NFC enabled device comes near capacitive NFC tag configured on packaged container.

9 Claims, 5 Drawing Sheets

(51) Int. Cl.
*H04B 5/22* (2024.01)
*H04B 5/70* (2024.01)

(56) References Cited

OTHER PUBLICATIONS

Escobedo, P. et al., “Flexible Strain and Temperature Sensing NFC Tag for Smart Food Packaging Applications”, IEEE Sensors Journal, Date: Jul. 2021, Publisher: IEEE, Link: https://ieeexplore.ieee.org/stamp/stamp.jsp?amumber=9502098.
Nguyen, Thanh-Binh et al., “Battery-Free and Noninvasive Estimation of Food pH and CO2 Concentration for Food Monitoring Based on Pressure Measurement”, Sensors (Basel), Date: Oct. 2020, Publisher: MDPI, Basel, Link: https://www.ncbi.nim.nih.gov/pmc/articles/PMC7589979/pdf/sensors-20-05853.pdf.
Rodriguez, Daniel et al., “A WPT/NFC-Based Sensing Approach for Beverage Freshness Detection Using Supervised Machine Learning”, IEEE Sensors Journal, vol. No. 21, Issue No. 1, Date: Jan. 2021, Publisher: IEEE, Link: https:/par.nsf.gov/servlets/purl/10230453.
Nguyen, Thanh-Binh et al., “Pressure Measurement-Based Method for Battery-Free Food Monitoring Powered by NFC Energy Harvesting”, Scientific Reports, Date: Nov. 2019, Publisher: Nature Publisher Group, Link: https://www.nature.com/articles/s41598-019-53775-1.pdf.
Kant, Rajni et al., “Radio frequency based sensor: An innovative detection tool for food spoilage”, The Pharma Innovation Journal, Date: 2017, vol. 6, Issue: 4, pp. 80-86, Publisher: The Pharma Journal, Link: https://www.thepharmajoumal.com/archives/2017/vol6issue4/PartB/6-4-5-781.pdf.
Kataria, Tejinder Kaur et al., “Dielectric characterization of raw and packed soy milks from 0.5 to 20 GHz at temperatures from 20 to 70 8C”, Journal of Food Science and Technology, Date: Aug. 2018, vol. 55, Issue: 8, pp. 3119-3126, Publisher: Association of Food Scientists & Technologists (India), Link: https://www.ncbi.nlm.nih.gov/pmc/articles/PMC6045991/pdf/13197_2018_Article_3238.pdf.

* cited by examiner

NON-INVASIVE METHOD AND SYSTEM FOR DETECTING QUALITY OF PACKAGED MILK

PRIORITY CLAIM

This U.S. patent application claims priority under 35 U.S.C. § 119 to: India Application No. 202221029274, filed on May 24, 2022. The entire contents of the aforementioned application are incorporated herein by reference.

TECHNICAL FIELD

The disclosure herein generally relates to milk quality estimation, and, more particularly, to a non-invasive method and a system for detecting quality of packaged milk.

BACKGROUND

A huge quantity of milk is lost or wasted everyday due to spoilage of milk before reaching the store or after reaching the consumer. Generally, milk remains fresh from few days to few months, depending upon the storage condition, processing technique and packaging of the milk.

Multilayer packaging (e.g., Tetra Pak™) is one of an innovative solution to address the problem of milk spoilage as it ensures milk remains fresh for a prolonged period of time without the use of preservatives and cold temperatures. But sometimes even with multilayer packaging, freshness of the stored milk cannot be guaranteed as the milk can get spoiled due to heat shock or damage of the packaging during transportation and distribution of the milk package.

Further, milk consumers generally consider date labels likes best-by' or 'use-by' before purchasing the milk and sometimes this act as a mental barrier that restricts them from buying the packaged milk near to use by date, thus leading to wastage of the milk even though the stored milk might be in good condition. In this scenario, the consumers may never come to know about the freshness of the milk until the packaging is opened.

Few devices that are available for milk quality detection include pH meter, milk quality tester, conductivity meter, electronic nose and the like. These devices are invasive in nature and cannot measure the milk quality without opening/damaging the milk pack. Further, some of the devices are very time taking as these require few mins to provide the results. Recently, some non-invasive quality sensors were introduced in the market. The non-invasive quality sensors measure milk quality indirectly through electrical/dielectric properties of the stored milk. However, these sensors are expensive and require complex fabrication as well as separate readers for milk quality estimation. Thus, a non-invasive and low cost milk quality detection technique that can detect the milk quality in real-time is preferred.

SUMMARY

Embodiments of the present disclosure present technological improvements as solutions to one or more of the above-mentioned technical problems recognized by the inventors in conventional systems. For example, in one aspect, there is provided a non-invasive method for detecting quality of packaged milk. The method comprises transmitting, via one or more hardware processors, a plurality of electromagnetic waves to a capacitive Near-field communication (NFC) tag configured on a packaged container containing milk using an NFC enabled device; obtaining, via the one or more hardware processors, a response of the capacitive NFC tag to the plurality of electromagnetic waves on the NFC enabled device, wherein the response is one of: a positive response; and a negative response, wherein the capacitive NFC tag is configured to give the positive response when a resonant frequency of the capacitive NFC tag is equal to a predefined frequency, and wherein the resonant frequency of the capacitive NFC tag becomes equal to the predefined frequency when a dielectric constant of the milk contained inside the packaged container is within a predefined range of a predefined critical dielectric constant of the milk; estimating, via the one or more hardware processors, quality of the milk contained inside the packaged container based on the obtained response; and displaying, via the one or more hardware processors, the quality of the milk on the NFC enabled device.

In another aspect, there is provided a system for detecting quality of packaged milk. The system comprises a memory storing instructions; one or more communication interfaces; and one or more hardware processors coupled to the memory via the one or more communication interfaces, wherein the one or more hardware processors are configured by the instructions to: transmit a plurality of electromagnetic waves to a capacitive Near-field communication (NFC) tag configured on a packaged container containing milk using an NFC enabled device; obtain a response of the capacitive NFC tag to the plurality of electromagnetic waves on the NFC enabled device, wherein the response is one of: a positive response; and a negative response, wherein the capacitive NFC tag is configured to give the positive response when a resonant frequency of the capacitive NFC tag is equal to a predefined frequency, and wherein the resonant frequency of the capacitive NFC tag becomes equal to the predefined frequency when a dielectric constant of the milk contained inside the packaged container is equal to a predefined critical dielectric constant of the milk; estimate quality of the milk contained inside the packaged container based on the obtained response; and display the quality of the milk on the NFC enabled device.

In yet another aspect, there are provided one or more non-transitory machine-readable information storage mediums comprising one or more instructions which when executed by one or more hardware processors cause a non-invasive method for detecting quality of packaged milk. The method comprises transmitting, via one or more hardware processors, a plurality of electromagnetic waves to a capacitive Near-field communication (NFC) tag configured on a packaged container containing milk using an NFC enabled device; obtaining, via the one or more hardware processors, a response of the capacitive NFC tag to the plurality of electromagnetic waves on the NFC enabled device, wherein the response is one of: a positive response; and a negative response, wherein the capacitive NFC tag is configured to give the positive response when a resonant frequency of the capacitive NFC tag is equal to a predefined frequency, and wherein the resonant frequency of the capacitive NFC tag becomes equal to the predefined frequency when a dielectric constant of the milk contained inside the packaged container is within a predefined range of a predefined critical dielectric constant of the milk; estimating, via the one or more hardware processors, quality of the milk contained inside the packaged container based on the obtained response; and displaying, via the one or more hardware processors, the quality of the milk on the NFC enabled device.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
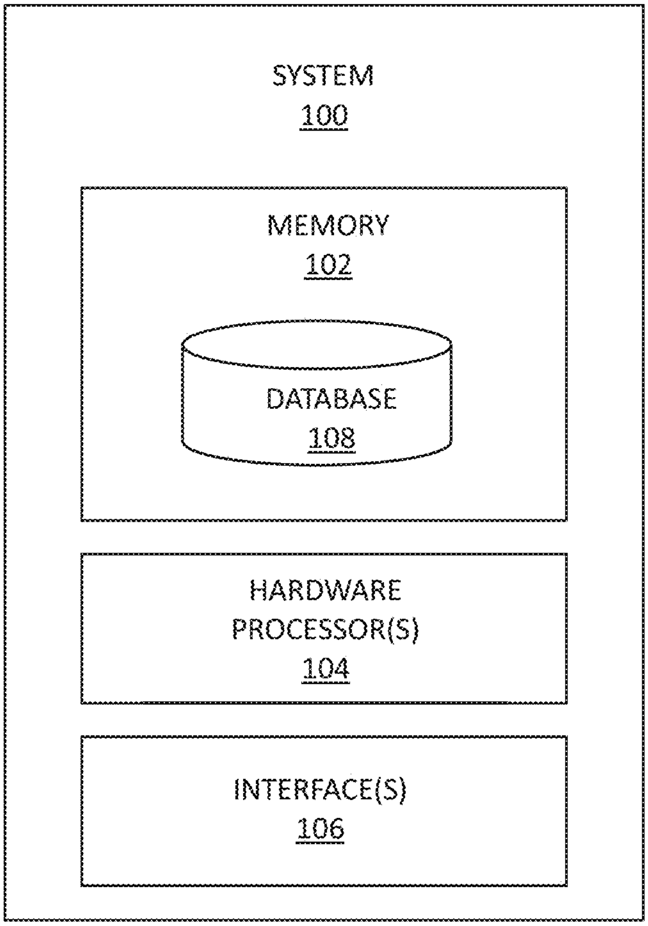
FIG. 1 illustrates an exemplary block diagram of a system for detecting quality of packaged milk, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Every year, globally around 128 million tons of produced milk is lost or wasted. In developed countries, more than 5% of total wastage of the milk occurs in the supply chain. As discussed earlier, freshness of the milk changes continuously with time i.e., the longer the duration of storage, the lower will be the freshness of milk. There are multiple reasons, such as milk contamination, improper storage, inefficient packaging etc., that lead to spoilage of milk. Different solutions, such as cold storage, addition of preservatives, heat treatment and innovative packaging (Tetra Pak™, plastic pouch, plastic, and glass container) have been developed to delay the degradation process of the milk. However, these solutions are proven to be less effective in reducing the spoilage of the milk as various factors, such as ambient conditions, damage in packaging etc., governs the quality of the packaged milk.

Generally, milk freshness is identified through primary tests, such as clot on boiling (COB) test, acidity test, methylene blue test, and the like. However, these tests are generally invasive in nature and require milk sample, laboratory analysis, skilled workforce, and long measurement time, thus making it difficult to measure the real-time freshness of milk during the supply chain when the packaging is intact.

Few temperature-time indicators, such as haptic labels are available in market for milk quality detection. But these labels are calibrated using only the temperature, and hence they cannot detect the actual/real-time changes that are occurring in the milk. Further, some non-invasive techniques such as ultrasonic, spectroscopy, etc. have also been used to detect quality of the milk, but they require sophisticated equipment, and skilled workforce. Also, these techniques fail to detect milk quality when packaging is opaque i.e., when the milk is packed in plastic pouch/container, cardboard packaging, aluminum foil packaging and multilayer packaging (Tetra Pak™). Hence, common methods that are used for detecting quality of milk cannot be easily used over the packaged milk. So, techniques that can ensure real-time detection of quality of the milk kept in packaged container is still to be explored.

Embodiments of the present disclosure overcome the above-mentioned disadvantages by providing a non-invasive method and a system for detecting quality of the packaged milk. More specifically, the system and the method of the present disclosure uses a sensing technique enabled in a capacitive Near-field communication (NFC) tag and an NFC enabled device for detecting quality of the packaged milk in real-time. In particular, the capacitive NFC tag is configured to provide milk quality information on the NFC enabled device when the NFC enabled device comes near the capacitive NFC tag configured on the packaged container.

For achieving this, a critical dielectric constant of the milk at spoilage is estimated using a dielectric constant estimation method and then the capacitive NFC tag specific to the packaged container is designed using the estimated critical dielectric constant of milk. The designed capacitive NFC tag is then configured on the packaged container. When the NFC enabled device comes near the capacitive NFC tag placed on the packaged container, the NFC tag is configured to give the positive response when a resonant frequency of the capacitive NFC tag is equal to a predefined frequency, and the resonant frequency of the capacitive NFC tag becomes equal to the predefined frequency when the dielectric constant of the milk contained inside the packaged container is within a predefined range of a predefined/pre-estimated critical dielectric constant of the milk.

In the present disclosure, the system uses the capacitive NFC tag configured on the packaged container for estimating quality of the milk kept in the packaged container, thereby ensuring real-time non-invasive estimation of the quality of the milk, while avoiding contamination of the milk during testing. Further, the system uses the NFC enabled device, such as smartphone for displaying the quality of the milk, thereby eliminating the need of requiring any skilled person for performing milk quality estimation. Additionally, the design of the capacitive NFC tag is very compact and handy, thereby making it usable for all kinds of packaging.

Referring now to the drawings, and more particularly to FIGS. 1 through 6, where similar reference characters denote corresponding features consistently throughout the figures, there are shown preferred embodiments and these embodiments are described in the context of the following exemplary system and/or method.

FIG. 1 illustrates an exemplary block diagram of a system 100 for detecting quality of packaged milk, in accordance with an embodiment of the present disclosure. In some embodiments, the system 100 may be implemented in a server system. In some embodiments, the system 100 may be implemented in a variety of computing systems, such as laptop computers, notebooks, hand-held devices, workstations, mainframe computers, and the like.

In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, a database 108 can be stored in the memory 102, wherein the database 108 may comprise, but are not limited to, a predefined frequency, a dielectric constant of fresh milk, a predefined critical dielectric constant of milk at spoilage, a predefined range of the predefined critical dielectric constant of the milk, a predefined dielectric constant calculation formula, a critical capacitance value of milk, one or more properties of a packaged container, and the like. The memory 102 further comprises (or may further comprise) information pertaining to input(s)/output(s) of each step performed by the system and method of the present disclosure. In other words, input(s) fed at each step and output(s) generated at each step are comprised in the memory 102 and can be utilized in further processing and analysis.

Figure 2:
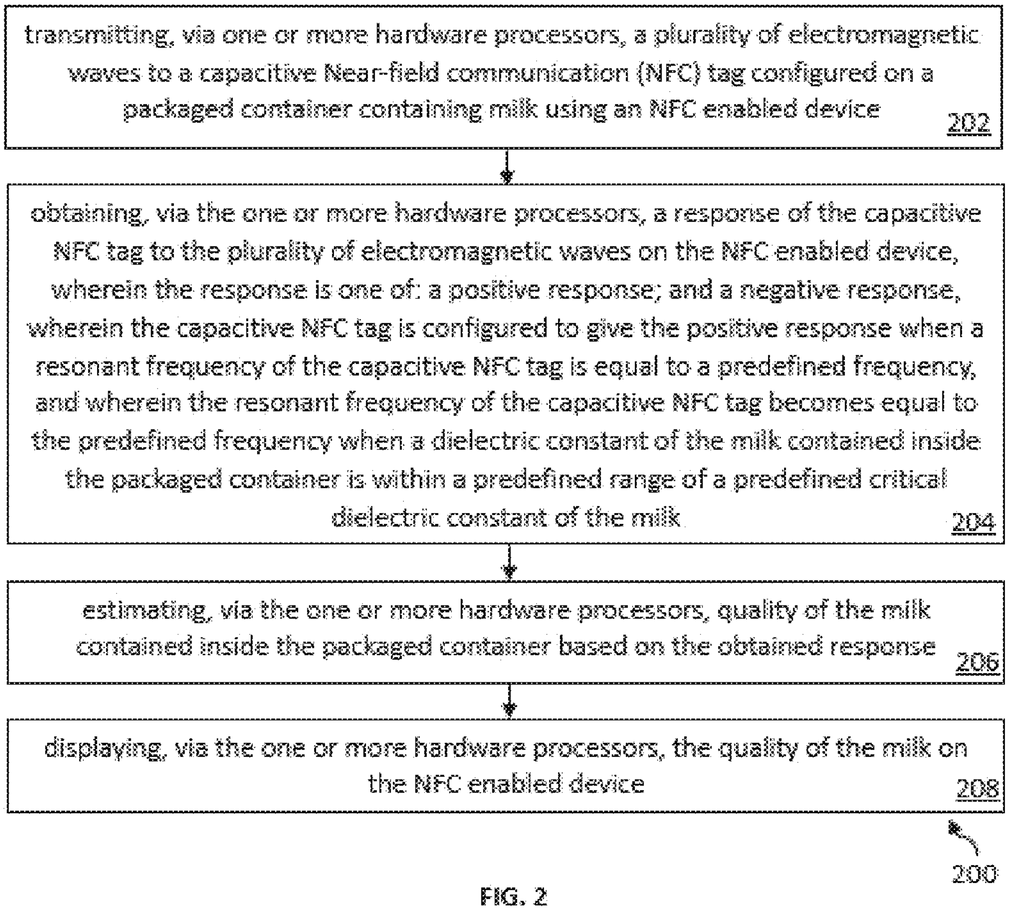
FIG. 2 illustrates an exemplary flow diagram of a non-invasive method for detecting quality of packaged milk, in accordance with an embodiment of the present disclosure.

FIG. 2, with reference to FIG. 1, illustrates an exemplary flow diagram of a method 200 for detecting quality of packaged milk, in accordance with an embodiment of the present disclosure. The method 200 may use the system 100 of FIG. 1 for execution. In an embodiment, the system 100 comprises one or more data storage devices or the memory 102 operatively coupled to the one or more hardware processors 104 and is configured to store instructions for execution of steps of the method 200 by the one or more hardware processors 104. The sequence of steps of the flow diagram may not be necessarily executed in the same order as they are presented. Further, one or more steps may be grouped together and performed in form of a single step, or one step may have several sub-steps that may be performed in parallel or in sequential manner. The steps of the method 200 of the present disclosure will now be explained with reference to the components of the system 100 as depicted in FIG. 1, and the flow diagram.

Figure 3A:
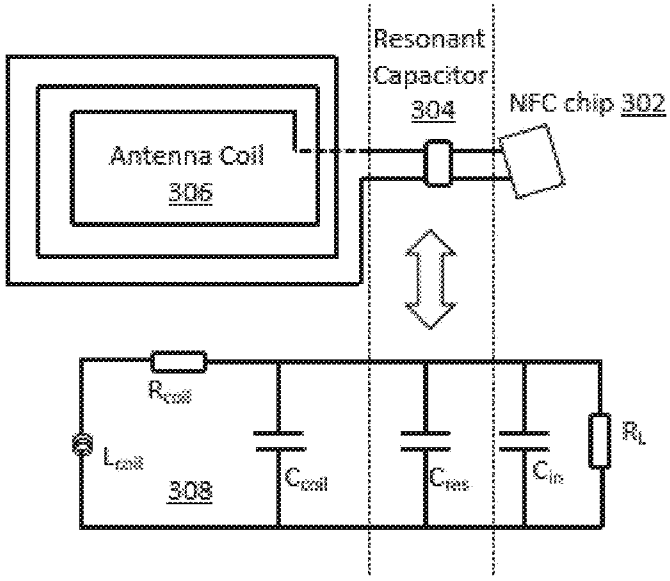
FIG. 3A illustrates an example representation of a Near-field communication (NFC) tag (known in prior art), in accordance with an embodiment of the present disclosure.
Figure 3B:
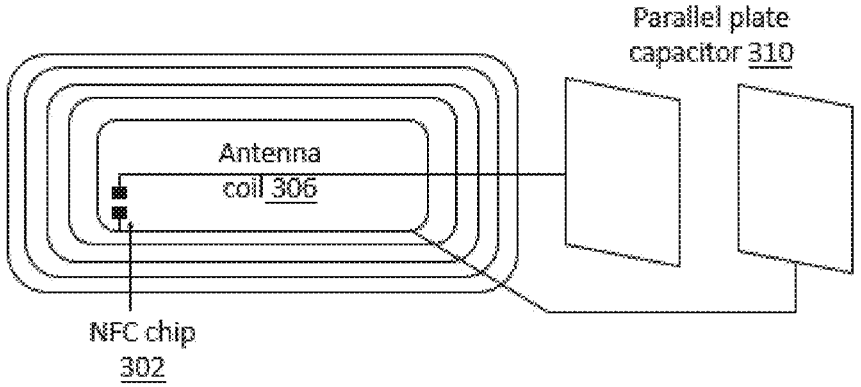
FIG. 3B illustrates an example representation of a capacitive NFC tag, in accordance with an embodiment of the present disclosure.
Figure 3C:
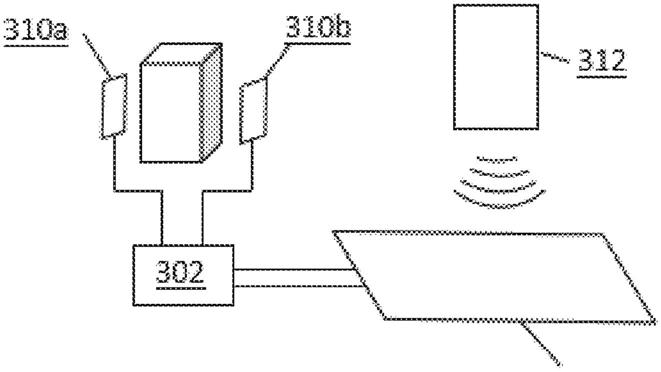
FIG. 3C illustrates a schematic representation of the capacitive NFC tag configured on a packaged container, in accordance with an embodiment of the present disclosure.

At step 202 of the method 200 of the present disclosure, the one or more hardware processors 104 comprised in the system 100 transmit a plurality of electromagnetic waves to a capacitive Near-field communication (NFC) tag configured on a packaged container 400/500 (shown with reference to FIGS. 4 and 5) containing milk using an NFC enabled device 312 (shown with reference to FIG. 3C). In an embodiment, the capacitive NFC tag may also be referred as tag and may be interchangeably used herein. Examples of the NFC enabled device 312 includes, but are not limited to, an NFC reader and a smartphone. More specifically, when the NFC enabled device scans or comes in contact with the capacitive NFC tag placed on the packaged container, the NFC enabled device 312 emits the plurality of electromagnetic waves that are transmitted to the capacitive NFC tag.

At step 204 of the method 200 of the present disclosure, the one or more hardware processors 104 of the system 100 obtain a response of the capacitive NFC tag to the plurality of electromagnetic waves on the NFC enabled device 312. In an embodiment, the response is one of a positive response, and a negative response. The above step can be better understood by way of following description.

The capacitive NFC tag is a passive tag that gets power from the electromagnetic waves that are emitted at a predefined frequency. In an embodiment, the predefined frequency is '13.56 MHz'. So, when the NFC enabled device transmits electromagnetic waves to the tag, the tag gets energized and provide a positive response on the NFC enabled device 312. It should be noted that the tag is configured in such a way that it gets energized only when a resonant frequency of the tag becomes equal to the predefined frequency, and the resonant frequency of the tag becomes equal to the predefined frequency only when a dielectric constant of the milk contained inside the packaged container is within a predefined range of a predefined critical dielectric constant of the milk.

In at least one example embodiment, the predefined critical dielectric constant of the milk is computed based on a critical capacitance value of the milk and one or more properties of the packaged container 400/500 using a predefined dielectric constant calculation formula. Further, the critical capacitance value of the milk is computed based on potential of hydrogen (pH) values of the milk and capacitance values of the milk contained inside the packaged container. Additionally, the predefined range of the predefined critical dielectric constant of the milk is computed based on the capacitance values of the milk.

To better understand the working of the capacitive NFC tag, first use of critical dielectric constant in estimating quality of the milk is explained and a dielectric constant estimation method that can be used for estimating dielectric constant of the milk at spoilage is also discussed below.

It is noted that, Potential of hydrogen (pH) is an important biochemical parameter and can be used as a quality indicator for a plurality of products, such as milk. In a study, it was found that the pH values of fresh raw milk range between 6.4 to 6.8 depending on the source of the milk. So, when the pH value of milk is greater than 6.3, it is considered as fresh milk and when the pH value of milk goes down below 6.3, the milk is considered as spoiled milk. So, pH value of '6.3' is found to be a critical value i.e., a borderline value in determining quality of the milk and thus used in determining the critical dielectric constant value of the milk at spoilage. In an embodiment, the dielectric constant estimation method is used for estimating critical dielectric constant of the milk at spoilage.

In one embodiment, as part of the dielectric constant estimation method, a packaged container, such as the packaged container 400/500 containing the milk is kept in a controlled environment and then one or more properties of the packaged container containing the milk are measured. The one or more properties include one or more of a dielectric constant of a material of the packaged container, a thickness of the material of the packaged container, a height of the packaged container, a length of the packaged container, a breadth of the packaged container, an area of the packaged container, a weight of the packaged container, and a size of the packaged container.

Thereafter, one or more capacitance plates of a predefined area are attached on at least one side of the packaged container. The capacitance plates attached on the at least one side of the packaged container are then connected with a capacitance meter that can measure capacitance value of the milk kept in the packaged container.

Then, pH values of the milk and the capacitance values of the milk kept in the packaged container are recorded at one or more time intervals using a pH meter and the capacitance meter, respectively, until the contained milk goes bad i.e., the milk gets spoiled and starts to smell. The measured pH values and the recorded capacitance values at the one or more time intervals are then used to compute the critical capacitance value of the milk using a pre-established pH-capacitance graph. More specifically, the value of critical capacitance ($C_{cr}$) corresponding to pH value of '6.3' is obtained from the pre-established pH-capacitance graph. Finally, the critical dielectric constant of the milk at spoilage is calculated based on the critical capacitance value of the milk and the one or more properties of the packaged container using a predefined dielectric constant calculation formula mentioned below:

$$\frac{1}{C_{cr}} = \frac{1}{C_j} + \frac{1}{C_m} + \frac{1}{C_j} \quad \text{Equation (1)}$$

$$\frac{1}{C_{cr}} = \frac{d_j}{A*\varepsilon_o\varepsilon_j} + \frac{d_m}{A*\varepsilon_o\varepsilon_{cr}} + \frac{d_j}{A*\varepsilon_o\varepsilon_j}, \quad \text{Equation (2)}$$

As can be seen in the predefined dielectric constant calculation formula, the properties of the packaged container ($\varepsilon_1$, $d_1$, $d_m$), capacitor plate area (A), critical capacitance of milk ($C_{cr}$) are all known variables and the only unknown is the critical dielectric constant $\varepsilon_{cr}$. So, $\varepsilon_{cr}$ can be estimated using the dielectric constant calculation formula. It should be noted that the value of the critical dielectric constant is dependent on the properties of the container and hence the value of the critical dielectric constant varies as per the packaged container.

So, once the value of the critical dielectric constant of the milk for the packaged container containing the milk is obtained, the same value may be used as a predefined critical dielectric constant of the milk by the system 100.

Additionally, depending upon the storage conditions and storage time of fresh milk, a dielectric constant of the fresh milk may not be always a single value and it may keep on varying in a small range before it reaches value of the critical dielectric constant of the milk at spoilage. For example, the capacitance value of fresh milk stored in a plastic container ranges from 40.5 pF to 41.8 pF and the corresponding dielectric constant is found to be in the range of 174-180. So, a range of the predefined critical dielectric constant of the milk is defined for detecting the quality of the milk. The same range is used as a predefined range of the predefined critical dielectric constant of the milk by the system 100.

Further, in real scenarios, milk can be stored in a packaged container made of different type of materials such as plastic, glass, aluminum, cardboard, etc., and that could have varying thicknesses and widths. The container material too has a specific dielectric constant value, thus designing the capacitive NFC tag specific to the packaged container used for containing milk is important. So, once the predefined range of the predefined critical dielectric constant of the milk is established, the system 100 creates the capacitive NFC tag specific to the packaged container using the predefined range of the predefined critical dielectric constant of the milk.

To create the capacitive NFC tag, the one or more hardware processors 104 of the system 100 first obtain an NFC tag and an NFC tag datasheet associated with the NFC tag. The NFC tag that is obtained here is a normal NFC tag that is existing in the art and the NFC tag datasheet is provided by the NFC tag manufacturer. In an embodiment, the NFC tag includes an NFC chip 302, a resonant capacitor 304, and an antenna coil 306 that are arranged in a circuit 308 (shown with reference to FIG. 3A). Thereafter, the system 100 accesses one or more circuit values of the circuit present in the obtained NFC tag from the NFC tag datasheet. The one or more circuit values includes one or more of a capacitance of the antenna coil $C_{coil}$, a resonant frequency $f_r$ of the NFC tag, a capacitance of the NFC chip $C_{in}$, and an inductance of the antenna coil $L_{coil}$.

In an embodiment, a capacitance of the NFC tag at the resonant frequency is calculated based on the one or more circuit values using a predefined resonant frequency calculation formula defined below:

$$f_r = \frac{1}{2\times\pi\times\sqrt{L_{coil}\times(C_{coil}+C_{res}+C_{in})}}$$

Where, $C_{res}$ represents capacitance of the NFC tag at the resonant frequency.

In a non-limiting example, when a commercially available NTAG216 NXP semiconductor tag is obtained by the system 100 for creating the capacitive NFC tag, the $C_{res}$ at the resonant frequency of 13.56 MHz is found to be 85.89 pF using the predefined resonant frequency calculation formula. This means, when the resonant capacitor present in the NFC tag has capacitance equal to 85.89 pF value, the NFC tag gets activated by coming in contact of the NFC enabled device 312.

In another embodiment, the capacitance of the NFC tag at the resonant frequency is provided by the NFC tag manufacturer and the capacitance value is present in the NFC tag datasheet. In that case, the system 100, instead of calculating, just access the capacitance of the NFC tag at the resonant frequency from the NFC tag datasheet.

Once the capacitance of the NFC tag at the resonant frequency is available, the system 100 determines whether a dielectric constant of a fresh milk (milk that is going to be packed in the packaged container) is in the predefined range of the predefined critical dielectric constant of the milk. This is done to check whether the dielectric constant of the fresh milk is a single value, or it keeps on varying in a small range. The dielectric constant of the fresh milk is accessed from the database 108.

In an embodiment, upon determining that the dielectric constant of the fresh milk is in the predefined range of the predefined critical dielectric constant of the milk, the system 100 determines an area of a parallel plate capacitor such that a capacitance value across one or more parallel plates of the parallel plate capacitor becomes equal to calculated capacitance of the NFC tag when the dielectric constant of the fresh milk becomes equal to the predefined critical dielectric constant of the milk contained in the packaged container using the predefined dielectric constant calculation formula (see equation 1 and equation 2).

More specifically, when the dielectric constant variation of the fresh milk is found to be in the small range and close to the predefined critical dielectric constant, the system 100 is configured to replace the resonant capacitor 304 present in the obtained NFC tag with a parallel plate capacitor 310 to make the capacitive NFC tag (shown with reference to FIG. 3B).

For performing replacement, the system 100 needs to determine the area to be maintained between parallel plates 310*a* and 310*b* (shown with reference to FIG. 3C) of the parallel plate capacitor 310 in such a way that the capacitance value across the parallel plates 310*a* and 310*b* becomes equal to calculated $C_{res}$ i.e., 85.89 pF when the dielectric constant of the fresh milk becomes equal to the predefined critical dielectric constant of the milk using the predefined dielectric constant calculation formula.

The properties of the packaged container used to hold milk ($\varepsilon_1$, $d_1$, $d_m$) and the value of the critical dielectric constant of milk $\varepsilon_{cr}$ are already available with the system 100. Using values for these variables ($\varepsilon_1$, $d_1$, $d_m$, $\varepsilon_{cr}$), the area of a capacitor (A) is estimated by the system 100. Thereafter, the system 100 uses the determined area to modify the NFC tag to obtain the capacitive NFC tag. The modification of the NFC tag includes replacing the resonant capacitor of the NFC tag with the parallel plate capacitor of the determined area to obtain the capacitive NFC tag. The parallel plate capacitor is configured to make the resonant frequency of the capacitive NFC tag equal to a predefined frequency when the dielectric constant of the milk contained in the packaged container is equal to the predefined critical dielectric constant of the milk i.e., with reference to the exemplary NFC tag obtained previously, the parallel plate capacitor of the estimated area will make the frequency equal to 13.56 MHz when the dielectric constant of the milk becomes equal to the predefined critical dielectric constant of the milk.

In at least one example embodiment, the packaged container containing the milk can be made of a plurality of layers of different materials of varying dielectric constant and thickness. In that case of multi-layer packaging, the system uses a modified dielectric constant calculation formula defined below:

$$\frac{1}{C_{res}} = \frac{1}{C_{j1}} + \frac{1}{C_{j2}} + \dots \frac{1}{C_{jn}} + \frac{1}{C_m} + \frac{1}{C_{j1}} + \frac{1}{C_{j2}} + \dots + \frac{1}{C_{jn}}$$

Where, $C_{ji}$ represents the capacitance corresponding to ith layer and n is the total number of layers present in the packaged container.

Upon determining that the dielectric constant of the fresh milk is not in the predefined range of the predefined critical dielectric constant of the milk i.e., the dielectric constant of fresh milk is not always a single value rather it keeps on varying in a small range before it reaches the critical value of spoilage, the one or more hardware processors 104 of the system 100 calculate a minimum area fora movable plate capacitor based, at least in part on, the one or more container properties of the packaged container and the predefined critical dielectric constant of the milk using a predefined minimum area calculation formula defined below:

$$\frac{1}{C_{res}} = \frac{d_j}{A_{min} * \varepsilon_o \varepsilon_j} + \frac{d_m}{A_{min} * \varepsilon_o * \text{maximum value in predefined range}} + \frac{d_j}{A_{min} * \varepsilon_o \varepsilon_j},$$

Where, $A_{min}$ represents minimum area of overlapping between a fixed plate and a moving plate of the movable plate capacitor.

Thereafter, the one or more hardware processors 104 of the system 100 calculate a maximum area for the movable plate capacitor based, at least in part on, the one or more container properties of the packaged container and the predefined critical dielectric constant of the milk using a predefined maximum area calculation formula defined below:

$$\frac{1}{C_{res}} = \frac{d_j}{A_{max} * \varepsilon_o \varepsilon_j} + \frac{d_m}{A_{max} * \varepsilon_o * \text{minimum value in predefined range}} + \frac{d_j}{A_{max} * \varepsilon_o \varepsilon_j}$$

Where, $A_{max}$ represents maximum area of overlapping between the fixed plate and the moving plate of the movable plate capacitor.

Once the minimum area and the maximum area for the movable plate capacitor are available, the one or more hardware processors 104 of the system 100 use the calculated minimum area and the maximum area to modify the NFC tag to obtain the capacitive NFC tag. The modification of the NFC tag includes replacing the resonant capacitor of the NFC tag with the movable plate capacitor to obtain the capacitive NFC tag. In an embodiment, the movable plate capacitor includes a fixed plate and a movable plate. The movable plate capacitor is configured in such a way that it makes the resonant frequency of the capacitive NFC tag equal to the predefined frequency when a moving area between the fixed plate and the movable plate of the movable plate capacitor is in between the calculated minimum area and the maximum area and the dielectric constant of the milk kept in the packaged container is in the predefined range of the predefined critical dielectric constant of the milk.

More specifically, when the dielectric constant of the fresh milk keeps on varying in a small range, the capacitive NFC tag should give the positive response for each of the values present in the small range. To achieve this, the system 100 uses the movable plate capacitor in the capacitive NFC tag. In the movable plate capacitor, the moving area of the capacitor plates is varied by sliding the movable plate present in the packaged container in a horizontal direction with respect to the fixed plate. So, when the moving area of the capacitor plates is in between the calculated minimum area and the maximum area and the dielectric constant of the milk kept in the packaged container is in the predefined range of the predefined critical dielectric constant of the milk, the resonant frequency of the capacitive NFC tag becomes equal to the predefined frequency. Thus, when the NFC enabled device 312 comes in contact with the capacitive NFC tag, the capacitive NFC tag provides the positive response.

In an embodiment, once the capacitive NFC tag is created by the system 100, the created capacitive NFC tag is placed at the packaged container.

At step 206 of the method 200 of the present disclosure, the one or more hardware processors 104 of the system 100 estimate the quality of the milk contained inside the packaged container based on the obtained response. As discussed earlier, the capacitive NFC tag is activated and provides a signal (also referred as the positive response) to the NFC enabled device 312 whenever the milk contained in the packaged container is fresh. So, if the positive response is received from the NFC tag, the quality of the milk is estimated as 'good' or 'fresh'. The capacitive NFC tag does not activate and hence no signal is received on the NFC enabled device 312 when the milk contained in the packaged container is spoiled. The no response obtained from the capacitive NFC tag is considered as the negative response and the quality of the milk contained inside the packaged container is estimated as 'bad' or spoiled'.

At step 208 of the method 200 of the present disclosure, the one or more hardware processors 104 of the system 100 display the quality of the milk on the NFC enabled device 312.

FIG. 3C illustrates a schematic representation of a capacitive NFC tag configured on a packaged container, in accordance with an embodiment of the present disclosure.

Figure 4:
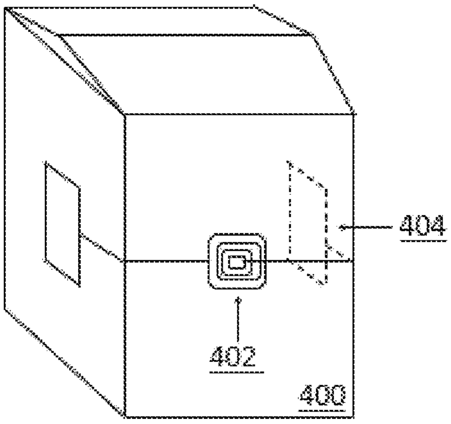
FIG. 4 illustrates an example representation of the capacitive NFC tag comprising a parallel plate capacitor configured on the packaged container, in accordance with an embodiment of the present disclosure.

FIG. 4, with reference to FIGS. 1 through 3C, illustrates an example representation of a capacitive NFC tag 402 comprising a parallel plate capacitor 404 configured on a packaged container 400, in accordance with an embodiment of the present disclosure.

As seen in the FIG. 4, the parallel plates are fixed on opposite sides of the packaged container 400 and a distance between parallel plates of the parallel plate capacitor is decided based on the calculated area.

Figure 5:
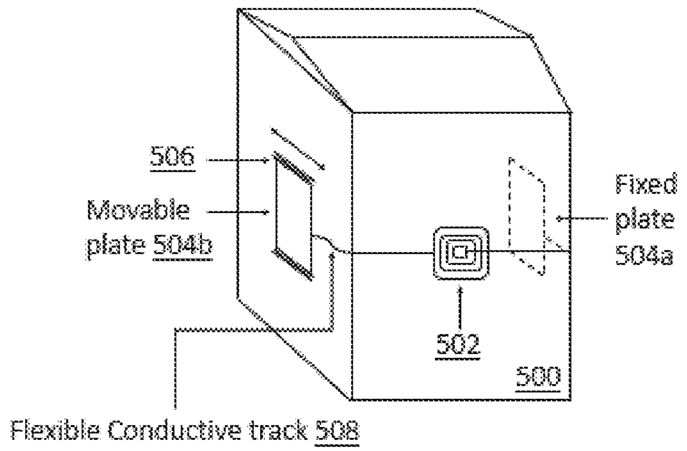
FIG. 5 illustrates an example representation of the capacitive NFC tag comprising a movable plate capacitor configured on the packaged container, in accordance with an embodiment of the present disclosure.

FIG. 5, with reference to FIGS. 1 through 4, illustrates an example representation of a capacitive NFC tag 502 comprising a movable plate capacitor configured on a packaged container 500, in accordance with another embodiment of the present disclosure.

As seen in the FIG. 5, the capacitive NFC tag 502 is attached on one side of the packaged container 500. A fixed plate 504*a* of the movable plate capacitor is fixed on one side of the packaged container 500 and a movable plate 504*b* of the movable plate capacitor is provided in a slot 506. The movable plate 504*b* is connected to the NFC tag 502 using a flexible conductive track 508 that can move with movement of movable plate 504*b*. The movable plate 504*b* is configured to move only in horizontal direction i.e., forward and backward direction. So, when the movable plate 504*b* slides from extreme left to right in the slot 506 it covers the maximum area to minimum area, and hence provides the response on the NFC enabled device 312.

Figure 6:
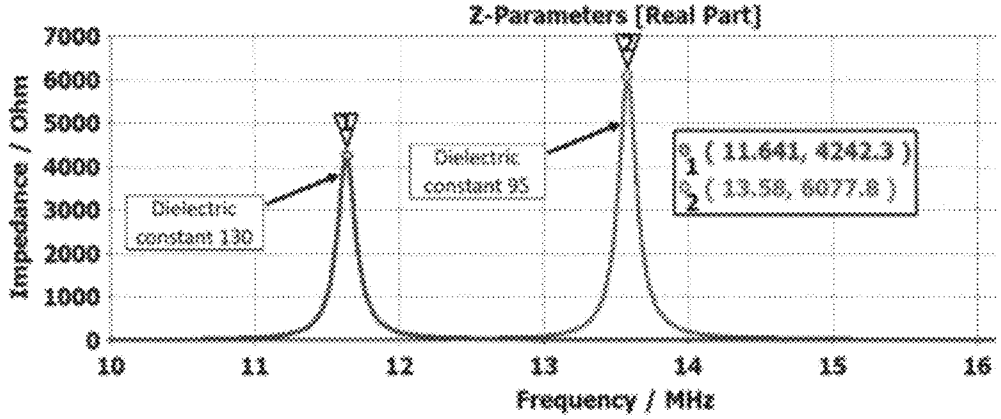
FIG. 6 is a graphical representation illustrating change in a frequency and a dielectric constant of milk with a change in quality of the milk, in accordance with an embodiment of the present disclosure.

FIG. 6 is a graphical representation illustrating change in a frequency and a dielectric constant of milk with a change in quality of the milk, in accordance with an embodiment of the present disclosure.

As can be seen in FIG. 6, when the quality of the milk is good, the value of the dielectric constant of milk and the frequency of the capacitive NFC tag is found to be '95' and '13.58', respectively. When the milk goes bad/spoiled, the value of the dielectric constant of milk and the frequency of the capacitive NFC tag is changed to '130' and '11.64', respectively. Hence, it is proven that the quality of the milk impacts the dielectric constant of milk which further impacts the frequency of the capacitive NFC tag, and thus the use of the dielectric constant for detecting the quality of the milk using the capacitive NFC tag is testified.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

As discussed earlier, available milk quality detection techniques fail to detect milk quality when packaging is opaque i.e., when the milk is packed in plastic pouch/container, cardboard packaging, aluminum foil packaging and multilayer packaging. Hence, common methods that are used for detecting quality of milk cannot be easily used over the packaged milk. To overcome the disadvantages, embodiments of the present disclosure provide a non-invasive method and a system for detecting quality of packaged milk. More specifically, the system uses the capacitive NFC tag configured on the packaged container for estimating quality of the milk kept in the packaged container, thereby ensuring real-time non-invasive estimation of the quality of the milk, while avoiding contamination of the milk during testing. Further, the system uses the NFC enabled device, such as smartphone for displaying the quality of the milk, thereby eliminating the need of requiring any skilled person for performing milk quality estimation. Additionally, the design of the capacitive NFC tag is very compact and handy, thereby making it usable for all kinds of packaging.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method comprising:

(i) transmitting a plurality of electromagnetic waves to a capacitive Near-field communication (NFC) tag disposed on a packaged container containing milk using an NFC enabled device and one or more hardware processors;

(ii) obtaining, using the one or more hardware processors, a response signal from the capacitive NFC tag in response to the plurality of electromagnetic waves transmitted to NFC tag, wherein the response signal is one of a positive response and a negative response; and the positive response is indicative of a resonant frequency of the capacitive NFC tag being equal to a predefined frequency when a dielectric constant of the milk contained inside the packaged container is within a predefined range of a predefined critical dielectric constant of the milk defined using a critical capacitance value of the milk, one or more properties of the packaged container, and a predefined dielectric constant calculation formula;

the critical capacitance value of the milk depends on potential of hydrogen (pH) values of the milk and capacitance values of the milk contained inside the packaged container;

the predefined range of the predefined critical dielectric constant of the milk depends on the capacitance values of the milk; and the negative response is indicative of the resonant frequency of the capacitive NFC not being equal to the predefined frequency;

the method further comprising:

(iii) determining, via the one or more hardware processors, quality of the milk contained inside the packaged container based on the obtained response signal; and (iv) displaying, via the one or more hardware processors, the quality of the milk on the NFC enabled device.

2. The processor implemented method of claim 1, further comprising:

creating, via the one or more hardware processors, the capacitive NFC tag specific to the packaged container using the predefined range of the predefined critical dielectric constant of the milk by:

obtaining, via the one or more hardware processors, an NFC tag and an NFC tag datasheet associated with the NFC tag, the NFC tag comprising an NFC chip, a resonant capacitor, and an antenna coil arranged in a circuit;

accessing, via the one or more hardware processors, one or more circuit values of the circuit present in the NFC tag from the NFC tag datasheet, wherein the one or more circuit values comprises one or more of: a capacitance of the antenna coil, a resonant frequency of the NFC tag, a capacitance of the NFC chip and an inductance of the antenna coil;

calculating, via the one or more hardware processors, a capacitance of the NFC tag at the resonant frequency based on the one or more circuit values using a predefined resonant frequency calculation formula;

determining, via the one or more hardware processors, whether a dielectric constant of a fresh milk is in the predefined range of the predefined critical dielectric constant of the milk, wherein the dielectric constant of the fresh milk is accessed from a database;

upon determining that the dielectric constant of the fresh milk is in the predefined range of the predefined critical dielectric constant of the milk, determining, via the one or more hardware processors, an area of a parallel plate capacitor such that a capacitance value across one or more parallel plates of the parallel plate capacitor becomes equal to calculated capacitance of the NFC tag when the dielectric constant of the fresh milk becomes equal to the predefined critical dielectric constant of the milk contained in the packaged container using the predefined dielectric constant calculation formula; and using, via the one or more hardware processors, the determined area to modify the NFC tag to obtain the capacitive NFC tag, wherein the modification of the NFC tag comprises replacing the resonant capacitor of the NFC tag with the parallel plate capacitor of the determined area to obtain the capacitive NFC tag, and wherein the parallel plate capacitor is configured to make the resonant frequency of the capacitive NFC tag equal to the predefined frequency when the dielectric constant of the milk contained in the packaged container is equal to the predefined critical dielectric constant of the milk.

3. The processor implemented method as claimed in claim 2, wherein upon determining that the dielectric constant of the fresh milk is not in the predefined range of the predefined critical dielectric constant of the milk:

calculating, via the one or more hardware processors, a minimum area for a movable plate capacitor based, at least in part on, one or more container properties of the packaged container and the predefined critical dielectric constant of the milk using a predefined minimum area calculation formula;

calculating, via the one or more hardware processors, a maximum area for the movable plate capacitor based, at least in part on, the one or more container properties of the packaged container and the predefined critical dielectric constant of the milk using a predefined maximum area calculation formula; and using, via the one or more hardware processors, the calculated minimum area and the maximum area to modify the NFC tag to obtain the capacitive NFC tag, wherein the modification of the NFC tag comprises replacing the resonant capacitor of the NFC tag with the movable plate capacitor to obtain the capacitive NFC tag, wherein the movable plate capacitor comprises a fixed plate and a movable plate, wherein the movable plate capacitor is configured to make the resonant frequency of the capacitive NFC tag equal to the predefined frequency when a moving area between the fixed plate and the movable plate of the movable plate capacitor is in between the minimum area and the maximum area and the dielectric constant of the milk kept in the packaged container is in the predefined range of the predefined critical dielectric constant of the milk.

4. A system comprising:

one or more communication interfaces;

one or more hardware processors; and a memory storing instructions, which when executed by the one or more hardware processors, cause the hardware processor to:

(i) transmit a plurality of electromagnetic waves to a capacitive Near-field communication (NFC) tag disposed on a packaged container containing milk using an NFC enabled device;

(ii) obtain a response signal from the capacitive NFC tag in response to the plurality of electromagnetic waves transmitted to NFC tag, wherein the response signal is one of: a positive response and a negative response; and the positive response is indicative of a resonant frequency of the capacitive NFC tag being equal to a predefined frequency when a dielectric constant of the milk contained inside the packaged container is within a predefined range of a predefined critical dielectric constant of the milk defined using a critical capacitance value of the milk, one or more properties of the packaged container, and a predefined dielectric constant calculation formula;

the critical capacitance value of the milk depends on potential of hydrogen (pH) values of the milk and capacitance values of the milk contained inside the packaged container;

the predefined range of the predefined critical dielectric constant of the milk depends on the capacitance values of the milk; and the negative response is indicative of the resonant frequency of the capacitive NFC not being equal to the predefined frequency; and (iii) determine quality of the milk contained inside the packaged container based on the obtained response signal; and (iv) display the quality of the milk on the NFC enabled device.

5. The system of claim 4, wherein the instructions, when executed by the one or more hardware processors further causes the one or more hardware processes to create the capacitive NFC tag specific to the packaged container using the value of the critical dielectric constant of the milk by:

obtaining an NFC tag and an NFC tag datasheet associated with the NFC tag, the NFC tag comprising an NFC chip, a resonant capacitor, and an antenna coil arranged in a circuit; and accessing one or more circuit values of the circuit present in the NFC tag from the NFC tag datasheet, wherein the one or more circuit values comprises one or more of: a capacitance of the antenna coil, a resonant frequency of the NFC tag, a capacitance of the NFC chip and an inductance of the antenna coil;

calculating a capacitance of the NFC tag at a resonant frequency based on the one or more circuit values using a predefined resonant frequency calculation formula;

determining whether a dielectric constant of a fresh milk is in the predefined range of the predefined critical dielectric constant of the milk, wherein the dielectric constant of the fresh milk is accessed from a database;

upon determining that the dielectric constant of the fresh milk is in the predefined range of the predefined critical dielectric constant of the milk, determining an area of a parallel plate capacitor such that a capacitance value across one or more parallel plates of the parallel plate capacitor becomes equal to calculated capacitance of the NFC tag when the dielectric constant of the fresh milk becomes equal to the predefined critical dielectric constant of the milk contained in the packaged container using a predefined capacitance calculation formula; and using the determined area to modify the NFC tag, obtain the capacitive NFC tag, wherein the modification of the NFC tag comprises replacing the resonant capacitor of the NFC tag with the parallel plate capacitor of the determined area to obtain the capacitive NFC tag, and wherein the parallel plate capacitor is configured to make the resonant frequency of the capacitive NFC tag equal to the predefined frequency when the dielectric constant of the milk contained in the packaged container is equal to the predefined critical dielectric constant of the milk.

6. The system of claim 5, wherein the instructions, when executed by the one or more hardware processors further causes the one or more hardware processors, upon determining that the dielectric constant of the fresh milk is not in the predefined range of the predefined critical dielectric constant of the milk, to:

calculate a minimum area for a movable plate capacitor based, at least in part on, one or more container properties of the packaged container and the predefined critical dielectric constant of the milk using a predefined minimum area calculation formula;

calculate a maximum area for the movable plate capacitor based, at least in part on, the one or more container properties of the packaged container and the predefined critical dielectric constant of the milk using a predefined maximum area calculation formula; and using the calculated minimum area and the maximum area to modify the NFC tag, obtain the capacitive NFC tag, wherein the modification of the NFC tag comprises replacing the resonant capacitor of the NFC tag with the movable plate capacitor to obtain the capacitive NFC tag, wherein the movable plate capacitor comprises a fixed plate and a movable plate, wherein the movable plate capacitor is configured to make the resonant frequency of the capacitive NFC tag equal to the predefined frequency when a moving area between the fixed plate and the movable plate of the movable plate capacitor is in between the minimum area and the maximum area and the dielectric constant of the milk kept in the packaged container is in the predefined range of the predefined critical dielectric constant of the milk.

7. A non-transitory computer readable information storage medium comprising one or more instructions, which when executed by one or more hardware processors, cause the one or more hardware processors to:

(i) transmit a plurality of electromagnetic waves to a capacitive Near-field communication (NFC) tag disposed on a packaged container containing milk using an NFC enabled device;

(ii) obtain a response signal from the capacitive NFC tag in response to the plurality of electromagnetic waves transmitted to NFC tag, wherein the response signal is one of: a positive response and a negative response; and the positive response is indicative of a resonant frequency of the capacitive NFC tag being equal to a predefined frequency when a dielectric constant of the milk contained inside the packaged container is within a predefined range of a predefined critical dielectric constant of the milk defined using a critical capacitance value of the milk, one or more properties of the packaged container, and a predefined dielectric constant calculation formula;

the critical capacitance value of the milk depends on potential of hydrogen (pH) values of the milk and capacitance values of the milk contained inside the packaged container;

the predefined range of the predefined critical dielectric constant of the milk depends on the capacitance values of the milk; and the negative response is indicative of the resonant frequency of the capacitive NFC not being equal to the predefined frequency; and (iii) determine quality of the milk contained inside the packaged container based on the obtained response signal; and (iv) display the quality of the milk on the NFC enabled device.

8. The non-transitory machine-readable information storage medium of claim 7, wherein the one or more instructions, when executed by one or more hardware processors, cause the one or more hardware processors to:

create the capacitive NFC tag specific to the packaged container using the predefined range of the predefined critical dielectric constant of the milk by:

obtaining an NFC tag and an NFC tag datasheet associated with the NFC tag, the NFC tag comprising an NFC chip, a resonant capacitor, and an antenna coil arranged in a circuit;

accessing one or more circuit values of the circuit present in the NFC tag from the NFC tag datasheet, wherein the one or more circuit values comprises one or more of: a capacitance of the antenna coil, a resonant frequency of the NFC tag, a capacitance of the NFC chip and an inductance of the antenna coil;

calculating a capacitance of the NFC tag at the resonant frequency based on the one or more circuit values using a predefined resonant frequency calculation formula;

determining whether a dielectric constant of a fresh milk is in the predefined range of the predefined critical dielectric constant of the milk, wherein the dielectric constant of the fresh milk is accessed from a database;

upon determining that the dielectric constant of the fresh milk is in the predefined range of the predefined critical dielectric constant of the milk, determining an area of a parallel plate capacitor such that a capacitance value across one or more parallel plates of the parallel plate capacitor becomes equal to calculated capacitance of the NFC tag when the dielectric constant of the fresh milk becomes equal to the predefined critical dielectric constant of the milk contained in the packaged container using the predefined dielectric constant calculation formula; and using the determined area to modify the NFC tag, obtaining the capacitive NFC tag, wherein the modification of the NFC tag comprises replacing the resonant capacitor of the NFC tag with the parallel plate capacitor of the determined area to obtain the capacitive NFC tag, and wherein the parallel plate capacitor is configured to make the resonant frequency of the capacitive NFC tag equal to the predefined frequency when the dielectric constant of the milk contained in the packaged container is equal to the predefined critical dielectric constant of the milk.

9. The non-transitory machine-readable information storage medium of claim 8, wherein the one or more instructions, when executed by one or more hardware processors, cause the one or more hardware processors, upon determining that the dielectric constant of the fresh milk is not in the predefined range of the predefined critical dielectric constant of the milk to:

calculate a minimum area for a movable plate capacitor based, at least in part on, one or more container properties of the packaged container and the predefined critical dielectric constant of the milk using a predefined minimum area calculation formula;

calculate a maximum area for the movable plate capacitor based, at least in part on, the one or more container properties of the packaged container and the predefined critical dielectric constant of the milk using a predefined maximum area calculation formula; and using the calculated minimum area and the maximum area, modify the NFC tag to obtain the capacitive NFC tag, wherein the modification of the NFC tag comprises replacing the resonant capacitor of the NFC tag with the movable plate capacitor to obtain the capacitive NFC tag, wherein the movable plate capacitor comprises a fixed plate and a movable plate, wherein the movable plate capacitor is configured to make the resonant frequency of the capacitive NFC tag equal to the predefined frequency when a moving area between the fixed plate and the movable plate of the movable plate capacitor is in between the minimum area and the maximum area and the dielectric constant of the milk kept in the packaged container is in the predefined range of the predefined critical dielectric constant of the milk.

* * * * *